(12) United States Patent
O'Mahony et al.

(10) Patent No.: US 7,886,611 B2
(45) Date of Patent: Feb. 15, 2011

(54) PRESSURE SENSOR DISCONNECT DETECTION FOR A BLOOD TREATMENT DEVICE

(75) Inventors: John J. O'Mahony, Maple Grove, MN (US); Mark Gelfand, New York, NY (US); Edwin B. Merrick, Stow, MA (US); Jayne B. Merrick, legal representative, Stow, MA (US)

(73) Assignee: CHF Solutions Inc., Brooklyn Park, MN (US)

( * ) Notice: Subject to any disclaimer, the term of this patent is extended or adjusted under 35 U.S.C. 154(b) by 0 days.

(21) Appl. No.: 12/688,161

(22) Filed: Jan. 15, 2010

(65) Prior Publication Data
US 2010/0175483 A1    Jul. 15, 2010

Related U.S. Application Data

(60) Division of application No. 11/193,423, filed on Aug. 1, 2005, now Pat. No. 7,647,834, which is a continuation of application No. 10/642,606, filed on Aug. 19, 2003, now Pat. No. 6,923,782, which is a division of application No. 09/833,798, filed on Apr. 13, 2001, now Pat. No. 6,773,412.

(51) Int. Cl.
*G01L 7/00* (2006.01)
(52) U.S. Cl. ............................. 73/756; 363/50; 324/537
(58) Field of Classification Search .................. None
See application file for complete search history.

(56) References Cited

U.S. PATENT DOCUMENTS

| | | | |
|---|---|---|---|
| 4,086,924 A | 5/1978 | Latham, Jr. | |
| 4,599,055 A | 7/1986 | Dykstra | |
| 4,657,529 A | 4/1987 | Prince et al. | |
| 4,784,768 A | 11/1988 | Mathieu | |
| 4,824,339 A | 4/1989 | Bainbridge et al. | |
| 4,936,980 A | 6/1990 | Yoshimichi et al. | |
| 5,114,580 A | 5/1992 | Ahmad et al. | |
| 5,312,550 A | 5/1994 | Hester | |
| 5,366,630 A | 11/1994 | Chevallet | |

(Continued)

FOREIGN PATENT DOCUMENTS

DE      26 44 062      9/1976

(Continued)

OTHER PUBLICATIONS

PRISMA, M60 Set, Instructions for Use.

(Continued)

*Primary Examiner*—Andre J Allen
(74) *Attorney, Agent, or Firm*—Nixon & Vanderhye P.C.

(57) ABSTRACT

A system is disclosed for detecting an electrical sensor, the system includes a sensor signal processing circuit further comprising an input port to receive a connector including the output signal lines of the sensor, a resistor connected to the output signal line of said input port, wherein the resistor is connected to a predetermined voltage; a sensor circuit having a connector adapted to connect to the connector, wherein the sensor circuit has a resistance substantially less than the pull-resistor, and the sensor signal processing circuit detects an unconnected sensor based on the voltage applied by the resistor.

14 Claims, 12 Drawing Sheets

U.S. PATENT DOCUMENTS

| | | | |
|---|---|---|---|
| 5,487,827 | A | 1/1996 | Peterson et al. |
| 5,536,237 | A | 7/1996 | Prince et al. |
| 5,653,887 | A | 8/1997 | Wahl et al. |
| 5,685,989 | A | 11/1997 | Krivitski et al. |
| 5,707,086 | A | 1/1998 | Treu et al. |
| 5,725,776 | A | 3/1998 | Kenley et al. |
| 5,730,712 | A | 3/1998 | Falkvall et al. |
| 5,762,805 | A | 6/1998 | Truitt et al. |
| 5,776,345 | A | 7/1998 | Truitt et al. |
| 5,906,589 | A | 5/1999 | Gordon et al. |
| 5,910,252 | A | 6/1999 | Truitt et al. |
| 6,090,048 | A | 7/2000 | Hertz et al. |
| 6,146,523 | A | 11/2000 | Kenley et al. |
| 6,687,140 | B2 * | 2/2004 | Kitamura ............... 363/50 |
| 7,057,396 | B2 * | 6/2006 | Nagase ............... 324/537 |
| 7,647,834 | B2 * | 1/2010 | O'Mahony et al. ........... 73/754 |
| 7,675,199 | B2 * | 3/2010 | Kuroda et al. ............... 307/125 |
| 7,747,807 | B2 * | 6/2010 | Komatsu et al. ........... 710/301 |
| 2001/0016699 | A1 | 8/2001 | Burbank et al. |
| 2001/0021817 | A1 | 9/2001 | Brugger et al. |
| 2001/0037079 | A1 | 11/2001 | Burbank et al. |
| 2001/0041892 | A1 | 11/2001 | Burbank et al. |
| 2002/0103453 | A1 | 8/2002 | Burbank et al. |
| 2002/0147423 | A1 | 10/2002 | Burbank et al. |
| 2003/0009123 | A1 | 1/2003 | Brugger et al. |
| 2003/0097087 | A1 | 5/2003 | Gura |
| 2003/0151934 | A1 * | 8/2003 | Kitamura ............... 363/50 |
| 2004/0189323 | A1 * | 9/2004 | Nagase ............... 324/609 |
| 2008/0116752 | A1 * | 5/2008 | Kuroda et al. ............... 307/125 |

FOREIGN PATENT DOCUMENTS

| | | |
|---|---|---|
| EP | 0 274 178 | 7/1988 |
| EP | 0 990 444 A2 | 4/2000 |
| GB | 1 583 023 | 1/1981 |
| WO | WO 02/082971 A3 | 10/2002 |

OTHER PUBLICATIONS

International Search Report dated Mar. 31, 2003.

Strife, C.F. et al, "Experience With a Low Volume Ultrafiltration Cell in Small Children," Clinical Nephrology 8:410-413 (1977).

Lauer, A. et al, "Continuous Arteriovenous Hemofiltration in the Critically Ill Patient, Clinical Use and Operational Characteristics," Annals of Internal Medicine 99:455-460 (1983).

Verbanck, J. et al, "Pure Ultrafiltration by Repeated Puncture of a Peripheral Arm-Vein as Treatment of Refratory Edema", The International Journal of Artificial Organs, vol. 3, No. 6 (1980), pp. 342-343.

Silverstein et al, "Treatment of Severe Fluid Overload by Ultrafiltration," The New England Journal of Medicine, vol. 291, No. 15, Oct. 10, 1974, pp. 747-751.

Blake, P. et al, "Refractory Congestive Heart Failure: Overview and Application of Extracorporeal Ultrafiltration," Critical Care Nephrology, *Advances in Renal Replacement Therapy*, vol. 3, No. 2 (Apr. 1966), pp. 166-173.

Civati G. et al, "Haemofiltration Without Substitution Fluid," Proc. EDTA-ERA, vol. 21 (1984), pp. 441-446.

Jenkins, R.D. et al, "The Use of Continuous Arteriovenous Hemofiltration With Hemodialysis in a Newborn," Draft #6, Personal Communication, 1985 (6 pages).

Jacobs, C. et al, "Continuous Arteriovenous Hemofiltration," Replacement of Renal Function by Dialysis, $4^{th}$ Ed., (1996) pp. 391-397.

Gupta, B.B. et al, "High Shear Rate Hemofiltration: Influence of Fiber Dimensions and Shear Rates," Artificial Organs, International Society for Artificial Organs, vol. 13(2) (1989), pp. 97-102.

Rimondini, A. et al, "Hemofiltration as Short-Term Treatment for Refractory Congestive Heart Failure," The American Journal of Medicine, vol. 83, Jul. 1987, pp. 43-48.

Donato, L. et al, "Treatment of End-Stage Congestive Heart Failure by Extracorporeal Ultrafiltration," The American Journal of Cardiology, vol. 59, (Feb. 1, 1987), pp. 379 and 380.

L'Abbate, A. et al, "Ultrafiltration: A Rational Treatment for Heart Failure," Cardiology 1989; 76:384-390.

Chen, Y. et al, "Direct Peripheral Venopuncture: Another New Choice of Temporary Vascular Access", Renal Failure, 22(3), 369-377 (2000).

International Search Report dated Sep. 11, 2002.

Jonathan D. Sackner-Bernstein, MD et al., "How Should Diuretic-Refractory, Volume-Overloaded Heart Failure Patients Be Managed?" The Journal of Invasive Cardiology, vol. 15, No. 10 (Oct. 2003), pp. 585-590.

Brian E. Jaski, MD et al., "Peripherally Inserted Veno-Venous Ultrafiltration for Rapid Treatment of Volume Overloaded Patients", Journal of Cardiac Failure, vol. 9, No. 3, (Jun. 2003), pp. 227-231.

* cited by examiner

PRESSURE SENSOR DISCONNECT DETECTION FOR A BLOOD TREATMENT DEVICE

RELATED APPLICATIONS

This application is a divisional of U.S. patent application Ser. No. 11/193,423 filed Aug. 1, 2005 which is a continuation of U.S. application Ser. No. 10/642,606, filed Aug. 19, 2003, and which is a divisional of U.S. application Ser. No. 09/833,798 filed Apr. 13, 2001, now U.S. Pat. No. 6,773,412.

BACKGROUND OF THE INVENTION

This invention relates to the medical instruments for extracorporeal treatment of blood and user interfaces for such instruments. One embodiment of the invention relates to a user interface for medical instruments for Renal Replacement Therapy and Artificial Kidney therapies.

1. Renal Replacement Therapies

Renal Replacement Therapy (RRT) can be performed in specialized dialysis centers for treatment of chronic patients that have permanently lost kidney function and in hospitals for treatment of patients with a need for temporary replacement of renal function. Different modalities of Continuous Renal Replacement Therapy (CRRT) have been used to treat patients suffering from excess fluid overload and acute renal failure. In acute settings, CRRT has been performed using standard methods of hemodialysis and continuous arterio-venous hemofiltration (CAVH). More recently, continuous veno-venous hemofiltration (CVVH) has been used to reduce the complications associated with such issues as hemodynamic instability and need for arterial access. Regardless of the type of medical equipment used and the specific type of treatment performed, RRT requires establishing an extracorporeal blood circulation path that passes blood through a filtration device.

RRT performs two primary blood treatment functions: ultrafiltration (removal of water from blood plasma), and solute clearance (removal of different molecular weight substances from blood plasma). RRT involves the use of a filter in a blood circuit through which circulates extracorporeal blood temporarily withdrawn from a patient. The RRT filter, also called hemofilter or dialyzer, can be set up to perform either or both of these functions simultaneously, with or without fluid replacement, accounting for the various modes of renal replacement therapy. "Clearance" is a term that describes the removal of substances, both normal and waste product, from blood.

Ultrafiltration is the convective transfer of fluid out of a plasma compartment of a filter and through pores in the filter membrane. The pores of the filter membrane pass (filter) water, electrolytes and small and middle-sized molecules (up to 20,000 to 30,000 daltons) from the blood plasma. Large molecules, proteins blood cells and other large-sized plasma components (as well as a portion of the water and smaller components) do not pass through the filter membrane and remain in the plasma compartment of the blood circuit and are returned to the patient. The ultrafiltrate output (e.g., water extracted from the blood) from the filtration pores is similar to plasma, but without the plasma proteins or cellular components. Since the concentration of small solutes is the same in the ultrafiltrate as in the plasma, no clearance is obtained from the plasma, but fluid volume, e.g., water, is removed.

Dialysis is the diffusive transfer of small solutes out of a blood plasma compartment of a filter by diffusion across the filter membrane. This transfer occurs as a result of a concentration gradient, with diffusion occurring from the filter compartment with higher concentration (typically the blood compartment) to the filter compartment with lower concentration (typically the dialysate compartment). Since the concentration of solutes in the plasma decreases, clearance is obtained, but fluid may not be removed in dialysis. Ultrafiltration can be combined with dialysis to obtain both clearance and fluid removal from blood plasma.

Hemofiltration is the combination of ultrafiltration and fluid replacement in the treatment of blood. Typically, hemofiltration treating larger volumes of blood than is needed for fluid control. The replacement fluid contains electrolytes, but not other small molecules. Since the net effect of replacing fluid without small solutes and ultrafiltration of fluid with small solutes results in net removal of small solutes, clearance is obtained during hemofiltration.

2. Limitations of User Interface of Existing Devices for RRT

RRT devices use sets of disposable blood passage circuits (generally referred to as "disposables") generally including tubing, filters, catheters, sensors and connectors that form a fluid circuit and are in direct contact with the blood and the fluid removed from the blood. These disposables can be assembled from components made by various manufacturers. Some more expensive disposables such as dialyzers can be used several times to treat the same patient. In some cases, disposable sets come assembled and the user need only mount the disposable blood passage on an instrument and pumping machine, and then prime the blood passage with sterile saline solution prior to its use. When the RRT device is ready for use, it is connected to the network of disposable and fluid filled tubes and electronic sensors that include the disposable blood passageway.

Modern RRT devices are microprocessor controlled. The microprocessor operates pumps, reads sensors and communicates with the user via a user interface regarding the RRT treatment. In more advanced RRT devices, the user interface has a graphics display that may be a touch screen or have an associated keypad. By interacting with a display and keys, the user interface enables a user to control the RRT device and monitor its operation.

During the operation, the RRT device detects conditions that trigger alarms and require user intervention. These alarms may occur often. For example, joints between parts in the blood passage disposable can spring leaks, allowing the ingress of air and facilitating clotting. Clotting of blood often occludes the blood passages. These RRT devices incorporate pressure sensors that enable them to detect disconnection and occlusion of tubing and components of the blood circuit. Air and blood leak detectors are also used to detect other alarm conditions that require immediate action from the user.

To operate RRT devices, a high degree of skill is required from users to troubleshoot the causes of alarms and promptly rectify the condition that provoked the alarm. A quick response from the user is needed because the RRT device is usually stopped as a result of the alarm, and within minutes the blood in the circuit may coagulate. Generally, when an alarm condition occurs, a user will receive an alarm notification and an alarm code from the RRT device. For example, code "E001" may be displayed on a numeric display. The user will interpret this as an alarm code by remembering that "E001" is a particular alarm or by consulting a manual for the RRT device that defines the display codes for the device. In the latest generation of RRT machines, less cryptic text messages are presented that describe alarm conditions. Instead of flashing an alarm code E001, for example, the RRT device displays a message such as "Infusion Tubing Disconnected". This plain language alarm message methodology is effective, but is still not intuitive to less-trained operators of the RRT device. Also, in the global marketplace, confusion often results from a language barrier and non-English speaking operators have difficulty with English language messages.

U.S. Pat. No. 5,858,239 discloses a dialysis machine that has a graphics display where a user is assisted by simple pictograms similar to "icons" used by the commonly used Microsoft Windows™ personal computer operating system. Another user interface that makes use of graphical icons instead of or complimenting text messages is disclosed in U.S. Pat. No. 5,620,608 for a dialysis machine. Although these icons help a user of a dialysis device navigate through a menu system, they are not helpful in troubleshooting faults in the blood fluid path of the device. A graphics user interface for an aphaeresis blood processing apparatus using pictorials is disclosed in U.S. Pat. No. 5,653,887, which displays icons and a symbolic diagram of the apparatus with an arrow pointing towards an element (blood centrifuge) requiring user attention. However, the graphics user interfaces disclosed in the prior art lack the ability to clearly direct a user to the specific point in the blood fluid path where an occlusion has been detected or the blood flow continuity has been broken.

SUMMARY OF THE INVENTION

A new and improved graphical user interface (GUI) for a RRT machine has been developed that integrates pictograms that point the user to the exact location of a fault in the machine blood circuit or fluid path.

The GUI addresses the needs of fluid removal and dialysis users by providing an intuitive interface that includes a dynamic pictorial diagram of the RRT device. The diagram shows the device in outline form, and emphasizes the fluid path, e.g., series of disposable components through which various fluids flow during treatment. In RRT devices these fluids include the pathway for the patient's blood, and can additionally include fluid paths for ultrafiltrate, dialysate and replacement solution.

The GUI as disclosed here is directed to an RRT device, but can be used in assisting any treatment that involves extracorporeal circulation. Extracorporeal blood circulation involves the continuous withdrawal of blood from a patient, where the blood is processed outside of the patient and then returned to the patient. Examples of such treatments are blood aphaeresis, heart-lung machines, full or partial heart bypass and transfusion of blood.

The pictorial diagram of the fluid path on the GUI display is designed to primarily assist the operator of an RRT device in identifying the source of an alarm caused by a malfunction of the circuit. The GUI display also may be used to assist the operator in assembling the disposable blood circuit, mounting it on the RRT pumping device, threading the tubing of the circuit into roller pumps, and connecting sensors and de-bubbling components of blood passage to the RRT device.

The pictorial aid of the GUI shows various interconnected tubes, valves, pumps and sensors of the disposable extracorporeal circuit. Tube lines of different color can identify different fluids. For example, bloodlines made be red on the display, and dialysate lines yellow. During normal operation of the device, only the lines actively involved in a particular treatment will be displayed. For example, if a dialysate solution is not involved in a treatment (such as hemofiltration), the corresponding dialysate fluid lines will not be displayed. The direction of fluid flow may be indicated by arrows or by an animation of the displayed pictogram. The pump rotation and fluid motion can be animated on the display as can be the level of fluid in different reservoirs such as dialysate, replacement solution or effluent collection bags.

If a fault is detected by the RRT device at a particular point along the fluid path, the corresponding position of the fluid path as shown on the pictogram will be accentuated. The location of the fault can be a particular bloodline segment, a pump, a reservoir, a connector or a sensor. A sensor can be, for example, a pressure sensor, an air detector, a weight scale or a blood leak detector. The fluid path element that needs attention from user can be identified on the display by a change of color, flashing of a specific portion of the diagram or by changing shape of the displayed element. In addition, an arrow on the display can point to the element shown in the pictogram. Typically a message is displayed elsewhere on the graphics screen instructing the user how to rectify the problem. The pictogram is immediately responsive to user actions. For example, if a disconnected sensor symbol is being flashed to attract the user's attention, and the user re-connects it, the pictogram will immediately change to its normal state.

Another aspect of the proposed method is that it assists the operator in detecting tubes that are not properly inserted into sensor elements of the RRT device console. Voltage outputs from sensors, such as a photometric blood leak detector and an ultrasonic air detector, can be used to detect fluid tubes that are not properly inserted into the sensor or other components of the RRT device. The user attention of the operator will be attracted by the flashing element of the pictogram so that user could insert the tube into the sensor tubing receptacle. The pictorial element will immediately stop flashing if the condition is corrected.

BRIEF DESCRIPTION OF THE DRAWINGS

A preferred embodiment and best mode of the invention is illustrated in the attached drawings that are described as follows:

FIGS. 7 and 8 show two further sample screens of the LCD 127. Pictogram 601 shows a system with a detected blood leak into the ultrafiltrate line. This failure of the circuit is detected by the photometric blood leak detector. Because blood is detected in the ultrafiltrate line, the blood leak detector 602 on the pictogram is flashing. In addition, pictogram 603 shows the system has detected an occlusion in the blood infusion tubing between the blood pump and the return cannula in the vein in the patient's arm. The return bloodline 604 is flashing. Similarly, the pictogram may flash in alternating colors the infusion or withdrawal tubing to designate a location of a bloodline, where a leakage or occlusion of blood has been detected based on an analysis by the controller of pressure between the filter and infusion catheter or the filter and withdrawal catheter.

DESCRIPTION OF AN EMBODIMENT OF THE INVENTION

The preferred embodiment of the present invention is a Graphical User Interface (GUI) that is a part of a blood ultrafiltration system and is used with a single use disposable set for ultrafiltration of blood to treat fluid overload in patients in a hospital setting. The disposable ultrafiltration set and the system are disclosed in commonly-owned U.S. patent application Ser. No. 09/660,195 filed on Sep. 12, 2000 and U.S. patent application Ser. No. 09/696,642 filed on Oct. 26, 2000, which applications are incorporated herein by reference.

To remove excess fluid from the patient the ultrafiltration set is mountable on a system console that is equipped with two pumps. One pump moves and controls the flow rate of blood through the tubing and filter of the ultrafiltration set. The other pump moves and controls the flow rate of ultrafiltrate. The ultrafiltration set contains a disposable blood/ultrafiltrate fluids circuit with an integral blood separation filter and three integrated pressure sensors. When the set is assembled on the system and is connected to the patient, the set forms a fluids path for blood and ultrafiltrate. The system interfaces with the fluid path via sensors and pumps. The Graphical User Interface or GUI is an integral part of the system console. It is used to give the operator information about treatment and assist them in identifying faults in the fluid path and causes of alarms.

Figure 1:
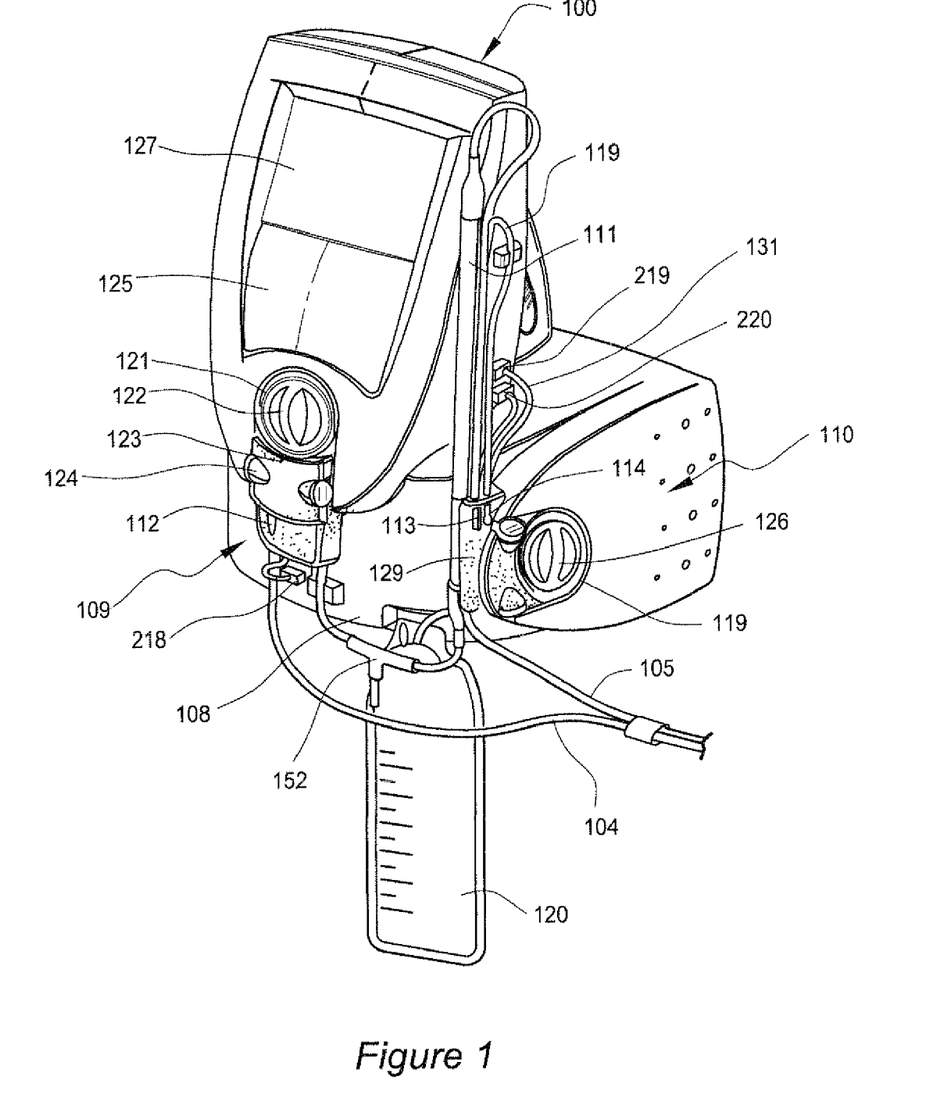
FIG. 1 is a perspective view of an intravenous blood ultrafiltration system using a disposable blood circuit and a user interface.
Figure 2:
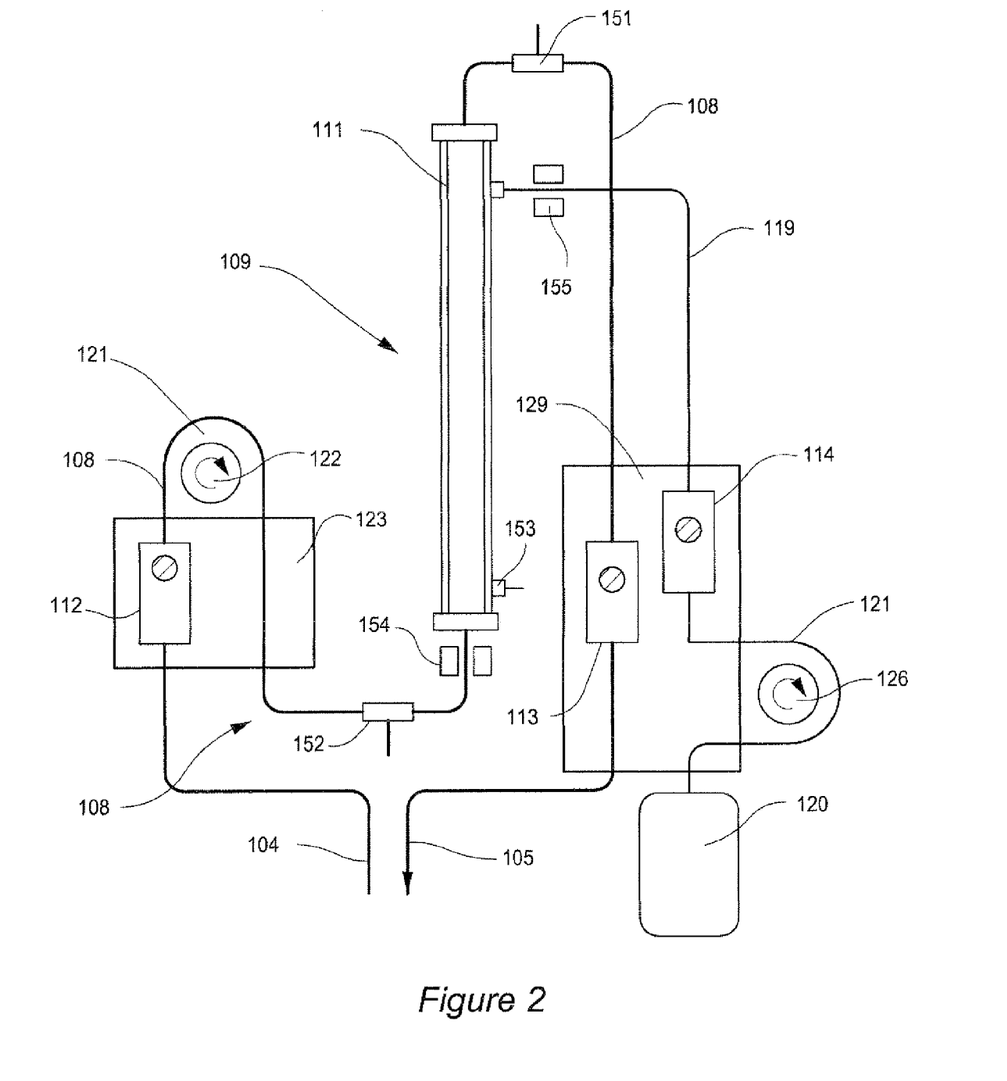
FIG. 2 is a schematic diagram showing a fluid path of blood and removed fluids for the blood circuit used with the ultrafiltration system shown in FIG. 1.

FIG. 1 shows an intravenous blood ultrafiltration system 100 for treating a patient (not shown) suffering from fluid overload. The system console 128 has a front panel with a membrane keypad 125 and a graphics display 127. To initiate ultrafiltration treatment, two plastic intravenous cannulae or needles are introduced into suitable peripheral veins of the patient for the withdrawal and return of the blood. The needles are attached to withdrawal tubing 104 and return tubing 105, and secured to skin with attachments, such as adhesive strips. The withdrawal and return tubing, 104 and 105, forms portions of a continuous blood fluid passage 108 that extends through a disposable blood circuit 109 (FIG. 2). The disposable blood circuit cartridge 109 is attached to a pumping system 110 to perform treatment.

Tubing sections of the blood circuit extend through cartridge 109, and form additional conduit links in the blood fluid passage 108. These tubing links are coupled to a blood filter 111 and blood pressure sensors 112, 113, that are contiguous with the tubing and form sections of the blood fluid passage 108. In other embodiments, the blood filter 111 may be supplied separately from other components of the blood circuit, and then the filter is connected to the blood circuit cartridge by the operator before treatment.

Figure 17:
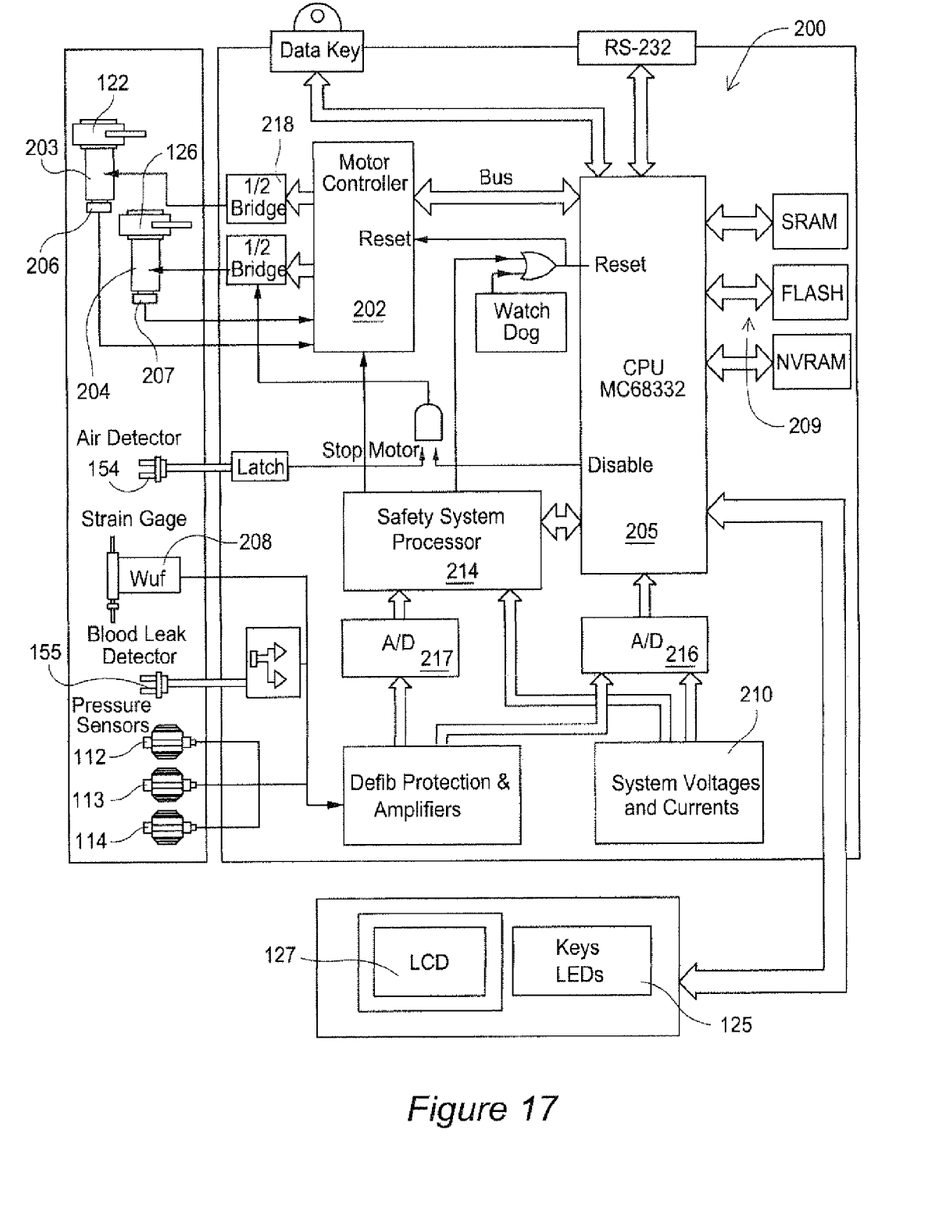
FIGS. 17 and 18 illustrate the electrical architecture of the ultrafiltration controller system.

The disposable blood ultrafiltration circuit cartridge may be supplied separate from the system, and packaged in a sterile package. The circuit is generally intended to be used for one single RRT treatment and is not reused. The cartridge is inserted into the pump system 110 by threading the tubing loops 121 in the blood passage 108, and ultrafiltrate discharge tubing 119 over the rims of roller pumps 122 and 126, respectively. As pumps 122 and 126 rotate, they slidably engage the tubing and force blood and ultrafiltrate fluids to move through the cartridge fluid passages. Microprocessor pump drivers control rotational speed of the pump and, thus, control the flow rate of the blood and ultrafiltrate through the fluid path. The pump drivers are part of system 110 and are controlled by a microprocessor controller within pump system 110 (FIG. 17).

The tubing of the blood circuit cartridge 109 may be mounted in a molded-plastic housing 123 that fits into a recess in the surface of system 110 and snaps into system 110 with latches 124. A blood withdrawal pressure sensor 112 is mounted to an inside surface of the cartridge housing 123. A pressure sensor 113 for the blood return tube 105 and an ultrafiltrate pressure sensor 114 are mounted to an inside surface of the second cartridge housing 129. Blood pressure sensors 112 and 113 and ultrafiltrate pressure sensor 114 include transducers that convert pressures into electrical signals carried by signal wires 131 that are connected to microprocessor controller in system 110 via the plug-in connectors 218, 219 and 220. Sensors 112, 113 and 114 may be model MPX2300 sensors manufactured by Motorola. Filter 111 in the may be a hemofilter having a polysulfone hollow fiber membrane available from Minntech of Minnesota.

The system console 128 has a front side having the display 127, keypad 125 and first roller pump 122. The console 128 also has a side, orthogonal to the front, which has the second roller pump 126. The blood circuit cartridge 109 is mounted on the console 128 by wrapping the blood circuit cartridge around the front and side of the console. Specifically, the tubing for the bloodline in the cartridge is inserted on the first roller pump 122. The filter 111 and tubing for the second roller pump 126 is attached to and mounted on the side of the console. By using both the front and side of the console to mount the blood cartridge, the front area of the console is substantially reduced. In particular, by folding the blood circuit around the front and side of the console, the area needed on the front face of the console to support the blood circuit is effectively reduced by one-half. Thus, the console can have a smaller front side and have a more compact and appealing appearance.

FIG. 2 is a schematic diagram of the blood and filtrate flow through the ultrafiltration system 100 known as a system flow path. The system symbolically depicted in the FIG. 2 is designed primarily to perform SCUF (Slow Continuous Ultrafiltration) but can be easily converted for other RRT treatment modalities. The port 153 of the hemofilter 111 is plugged for SCUF. If dialysis is desired, a source of dialysate fluid can be connected to this port 153. Dialysis fluid will circulate through the filter casing and interface with blood through the hollow fiber membrane so that clearance can be obtained via the diffusion of solute. For a dialysis mode, dialysate may circulate in a direction opposite to blood by reversing the pump 126. Alternatively the access port 152 in the circuit tubing 108 can be used to infuse the replacement solution. Ultrafiltration rate can be increased proportionally by speeding up the pump 122 so that clearance can be obtained by convective transport of solute with ultrafiltrate.

Similarly, the post-filter port 151 can be used to infuse the replacement solution if desired. With these additions (well known to persons of ordinary skill in the field of RRT), the described apparatus can be used to perform dialysis and hemofiltration.

Regardless of the RRT modality desired, the basic principles of the apparatus design remain the same. Blood that is withdrawn from the patient flows into the withdrawal tubing 104 and enters the blood passage 108 of the blood circuit. Blood passes through the hollow fibers of the filter 111, and is returned to the patient via the return tube 105. Ultrafiltrate, effluent or dialysis solution passes through the filter casing surrounding the blood filled hollow fibers. Prior to return, blood passes through the pressure sensor 113. Pump 122 generates and controls the flow of blood. Pump 126 generates and controls the flow of ultrafiltrate. Pump segment tubing loops 121 are attached to cartridges 123 and 129 to assist loading of pumps and prevent tubes from kinking. The ultrafiltrate line pressure sensor 114 is integrated into the same cartridge as the blood return sensor 113. Pressure sensors 112, 113 are integral to the blood passage 108 in the cartridges 123 and 129. These sensors are disposed in blood passage 108, such that a diaphragm of the sensor, which is the device that is in fluid contact with the load and directly responds to the blood pressure, is adjacent the blood passage.

From the blood pump 122 to the filter 111, blood traverses through an air detector sensor 154. The air detector sensor uses attenuation of ultrasonic sound waves in fluid to detect air bubbles in the blood passage 108. An air bubble indicates a leak or break in the blood circuit. An air bubble can be dangerous if passed into the bloodstream of the patient. Accordingly, the detection of an air bubble will cause an alarm and stop the pumps.

Similar to the blood pressure sensors in the blood passage of the circuit, the pressure sensor 114 (which may include a diaphragm in fluid contact with the filtered fluid) for the ultrafiltrate is integrally formed in the filtrate tubing 119 of the circuit between the filter 111 and the ultrafiltration bag 120. Ultrafiltrate exiting the filter 111 passes through the blood leak detector 155. The blood leak detector is a photometric device that uses infrared light beam to detect presence of red blood cells in the ultrafiltrate. The detection of blood in the ultrafiltrate line indicates a filter failure because blood cells should not normally pass through the filter membrane into the filtrate line.

The blood and ultrafiltrate pressure sensors 112, 113 and 114 are included in the disposable cartridge and are intended for one-time use. Air detector 154 and blood leak detector 155 are mounted on the system console and have means to clamp around the plastic tubing that forms the fluid passage. Infrared and ultrasonic waves can penetrate the plastic tubing wall.

The sensors each have a generally straight and hollow fluid passage that is coupled to the blood or filtrate tubing in the cartridge. The passages in the sensors are contiguous with the blood and ultrafiltrate passage of the cartridge.

The electrical signal is transmitted by the sensors to the pump system 110 through electrical signal lines, e.g., wires. A microprocessor controller (FIG. 11) in system 110 receives the pressure signals via the wire lines and determines the pressure level of the blood or ultrafiltrate in the fluid passage in which the associated sensor is positioned. Similarly the system receives information of presence of air in the blood flow or blood in ultrafiltrate.

Figure 3:
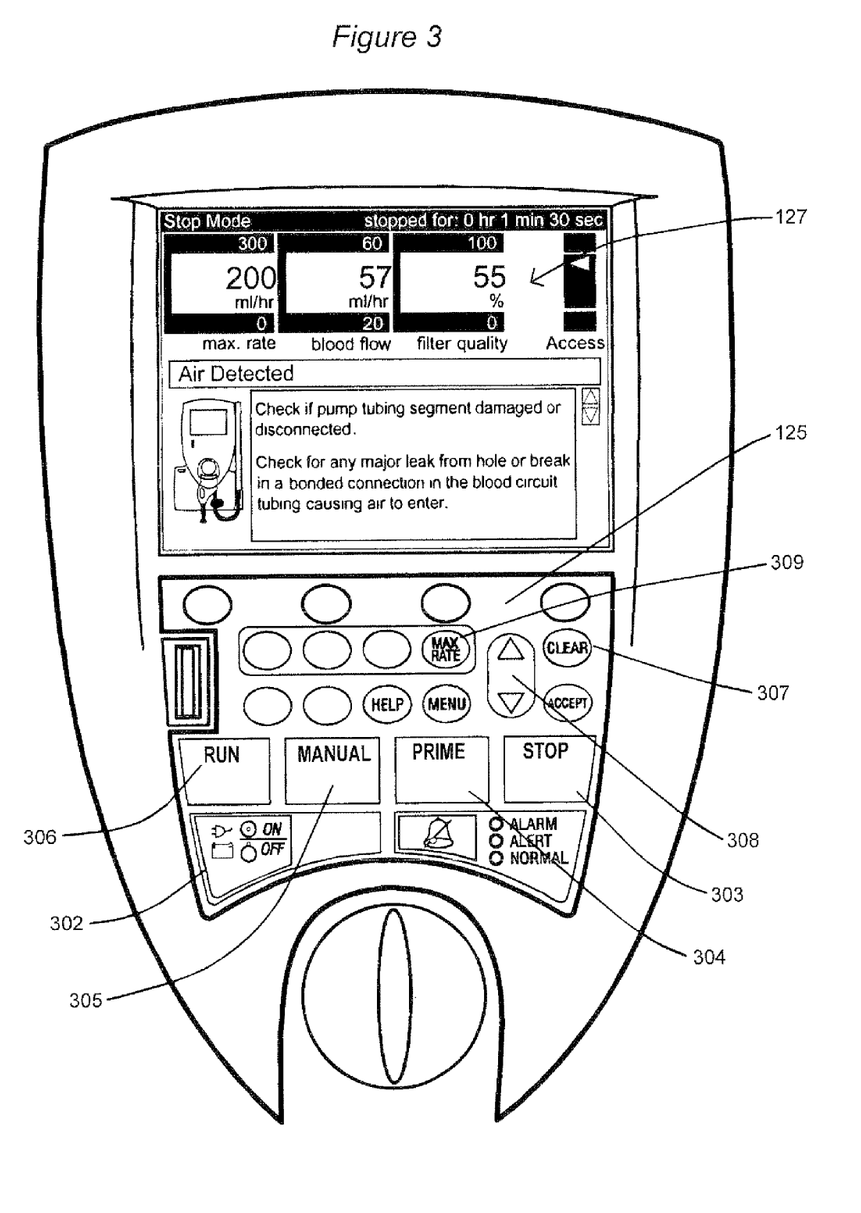
FIG. 3 is an enlarged view of the user interface area of the device shown in FIG. 1 with a graphics screen.

FIG. 3 illustrates one embodiment of the User Interface for the Ultrafiltration system 100. The membrane control panel 125 consists of 14 operational keys with 8 non-operational keys for future use. The membrane panel also displays information to the user regarding, for example:

The mode of operation (e.g., STOP, MANUAL, PRIME or RUN) via the status LEDs on the top left-hand corners of the corresponding key.

The status of the system, ALARM, ALERT or NORMAL via the status LEDs.

Whether ALARM SILENCE is active or not via the alarm silence LED.

The source of power via LED next to the battery and AC plug symbol.

Whether the device is powered ON or OFF.

The ON/OFF key 302 is used to power on the system. The key is in the ON position when one of the mode keys has an LED (light emitting diodes) are illuminated. A momentary press turns power ON but the key must be depressed for 0.5 seconds before the device can be powered OFF. When the green LED beside the plug symbol is lit it indicates that AC is the source of power. When the green LED beside the battery symbol is lit it indicates that battery is the source of power.

The STOP key 303 may be used to stop the system and is available in all modes. When the STOP key is activated, it immediately stops the rotation of the blood and ultrafiltrate pumps and thereby ceases the flow of blood and filtrate through the blood circuit. Upon power on, the STOP mode is the default mode. The PRIME mode 304 primes the circuit with saline so as to remove air from the circuit before connecting the catheters to the patient. In the PRIME mode, the system pumps saline for 2 minutes, and then must detect no air in the circuit for 40 seconds (while the saline flows) consecutively before PRIME is deemed successful.

The MANUAL mode 305 replaces the saline in the circuit with blood from the patient or to advance an air bubble. The MANUAL mode will begin immediately from STOP mode when the MANUAL key is pressed. To operate the system in MANUAL mode, the user has to continually press the MANUAL key. When the MANUAL key is released or a one-minute manual time-out period expires, the system will automatically enter the STOP Mode. The MANUAL key may only be accessed from the STOP mode and only if the PRIME mode has successfully completed. If the current mode is RUN mode, pressing the MANUAL key has no effect.

The RUN Mode 306 withdraws and infuses blood from and to the patient while performing ultrafiltration at the set MAX RATE. Ultrafiltration is performed when the blood flow exceeds 40 mL/min or some other minimal flow setting. The RUN key may be accessed from the STOP mode after the PRIME mode has successfully completed. The ACCEPT key confirms that the user intends to enter the PRIME mode or a particular MENU Function.

The CLEAR key 307 clears active alarms, clears the ALARM SILENCE function, clears an active request before it has been accepted and moves the display of selectable functions upwards in the menu level. If the alarm condition is still present, the alarm will re-annunciate after the CLEAR key has been pressed. If the PRIME key is pressed in error in STOP mode (active request), the CLEAR key can be used to clear the request and return the system to STOP mode. The UP and DOWN arrows 308 allow the user to scroll through the menu options, scroll help text, and increase and decrease user settings such as MAX RATE, Alarm Volume and Contrast. The MAX RATE key 309 allows the user to set the ultrafiltrate rate. The HELP key causes the display of information about the current state of the system. If pressed, the HELP key will display the function of the current mode when no alarms are present.

When pressed, the MENU key causes the display to show the following options: Alarm History, Change Date and Time, Change Alarm Volume, Disable Blood Leak Detector, View Software Revision.

The MENU options are available from all modes, STOP, PRIME, MANUAL and RUN.

When selected, the:

Alarm History option displays the last 10 active alarms along with the time of occurrence.

The Change Date and Time option allows the user to change the date and time.

The Change Alarm Volume allows the user to adjust the main alarm volume between 65 dBA and 80 dBA.

The Disable Blood Leak Detector allows the user to disable the blood leak detector.

The View Software Revision allows the user to see which software revision the system is running.

The Liquid Crystal Display (LCD) 127 may be a monochrome or color flat panel display. The LCD screen has a large viewing area, and improves the user friendliness of the device by providing helpful data to the user on how to solve each alarm condition.

Figure 4:
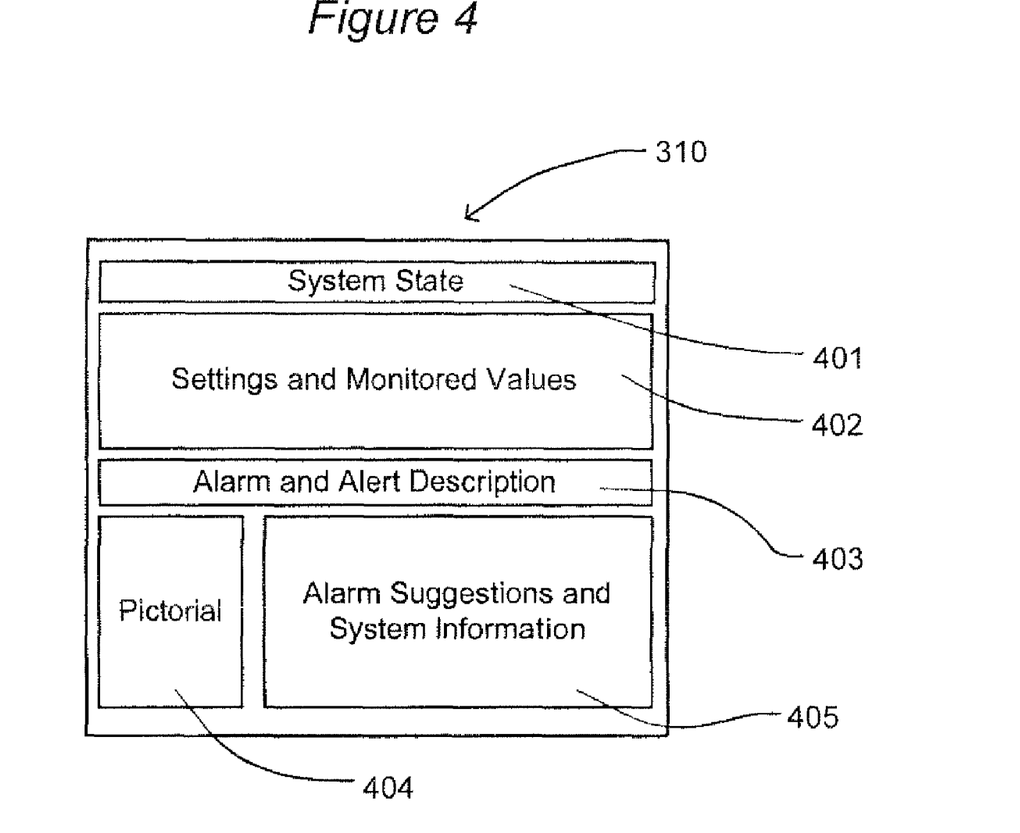
FIG. 4 is a schematic diagram of the LCD Screen layout.

FIG. 4 illustrates the information displayed on the LCD. The LCD screen 127 is divided into five areas. The system state area 401 shows the current system mode and length of time for that mode. The Settings and Monitored Values area 402 shows the user set MAX RATE and the actual blood flow in a manner that allows for comparison of these two flow rates. The Alarm and Alert Description area 403 displays the text of the active alarm. The Pictogram area 404 shows the affected system element, e.g., section of the blood circuit, to the user by flashing that affected section to draw the user's attention to the source of the alarm. The Alarm Suggestion and system Information area 405 displays suggested fixes for alarms. It is also used to display help and to navigate the user through the menu options.

Figure 5:
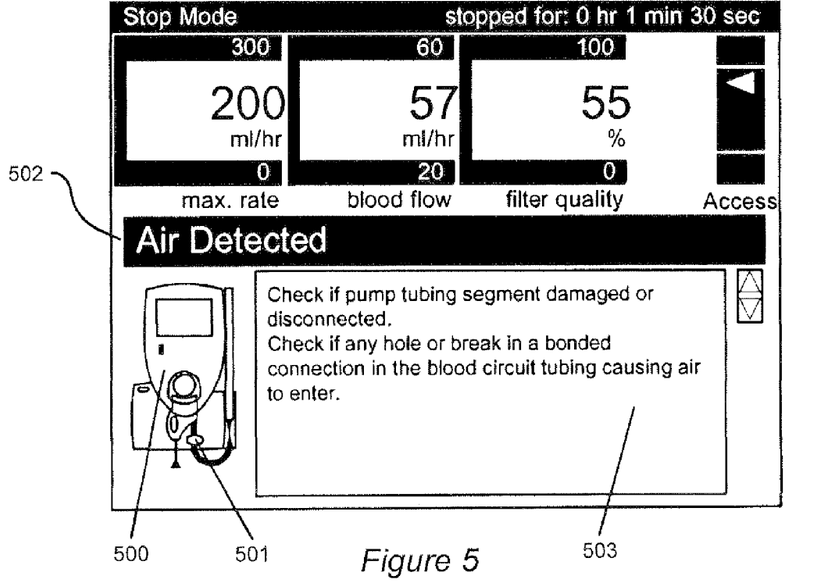
FIGS. 5 and 6 are examples of screens with pictograms indicating air detection and infusion disconnection faults.
Figure 6:
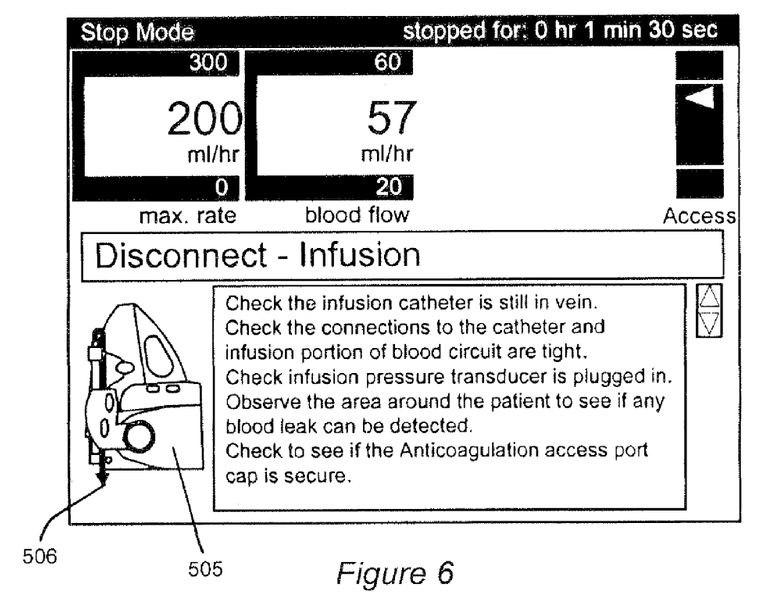

FIGS. 5 and 6 show two sample screens of the LCD screen 127. The air detector element 501 of the pictogram 500 is flashed to indicate the source of trouble. The error message 502 is also flashing (changing background color). User instructions 503 are displayed to the right of the pictogram. Pictogram 505 shows the ultrafiltration console 100 from the side. The alarm message 507 indicates that the blood infusion line that returns blood to the patient is disconnected. The blood return line 506 with an arrow at its termination is flashing to indicate to the user the location of the fault in the circuit.

Figure 7:
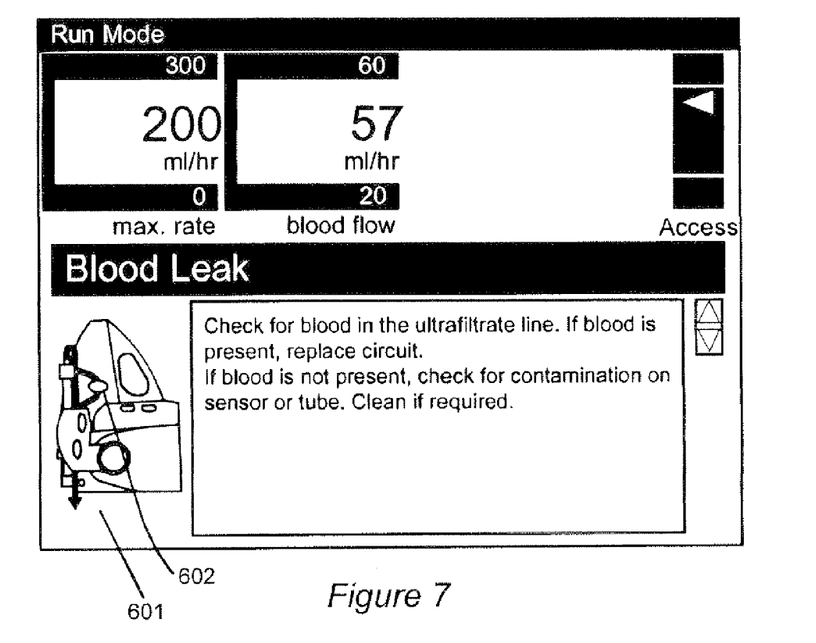
Figure 8:
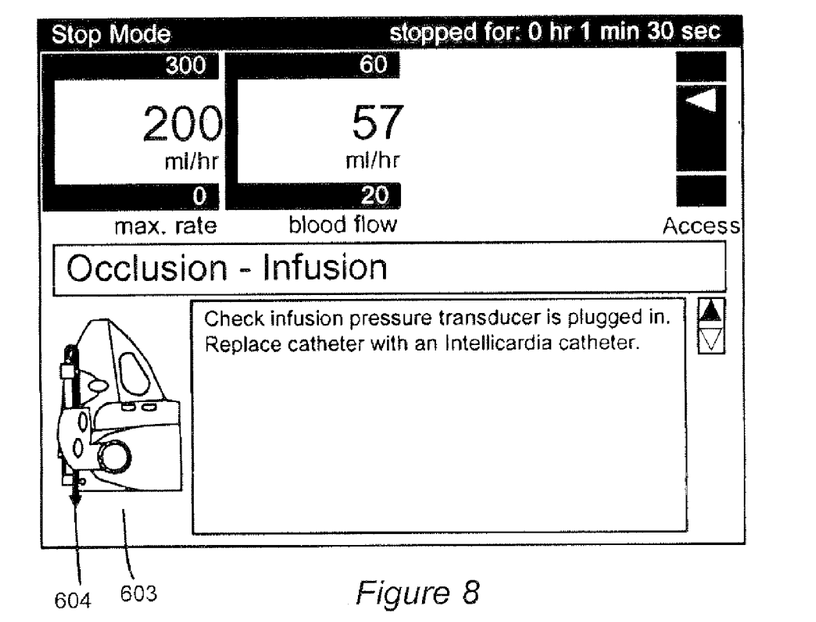

FIGS. 7 and 8 show two further sample screens of the LCD 127. Pictogram 601 shows a system with a detected blood leak into the ultrafiltrate line. This failure of the circuit is detected by the photometric blood leak detector. Because blood is detected in the ultrafiltrate line, the blood leak detector 602 on the pictogram is flashing. In addition, pictogram 603 shows the system has detected an occlusion in the blood infusion tubing between the blood pump and the return cannula in the vein in the patient's arm. The return bloodline 604 is flashing.

Figure 9:
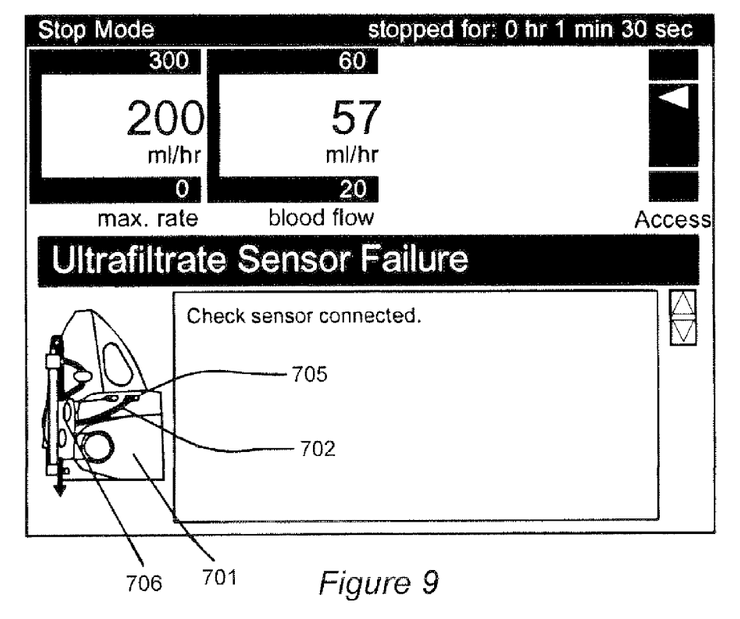
FIGS. 9 and 10 are examples of screens with pictograms indicating ultrafiltrate sensor failure and withdrawal bloodline disconnection faults.
Figure 10:
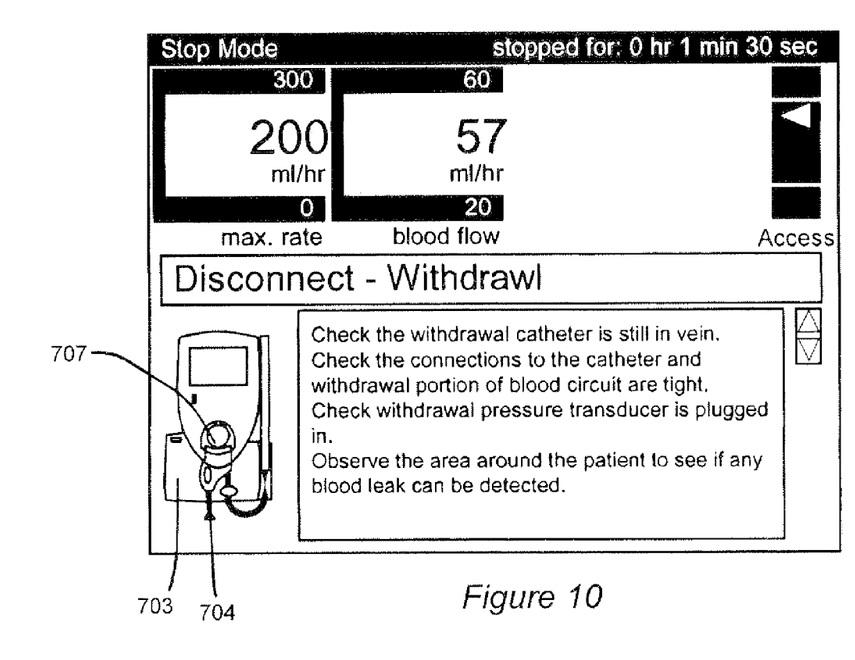

FIGS. 9 and 10 show another two sample screens with the pictogram. Pictogram 701 shows a system that has detected a disconnected ultrafiltrate pressure sensor. The lead wire 702 that connects the pressure sensor 706 in the disposable cartridge to the connector 705 on the console is the pictogram element flashing. Pictogram 703 shows the frontal view of the system with the blood withdrawal line 704 flashing. The error detected by the system is a disconnection in the blood withdrawal line between the patient and the blood pump 707.

Figure 11:
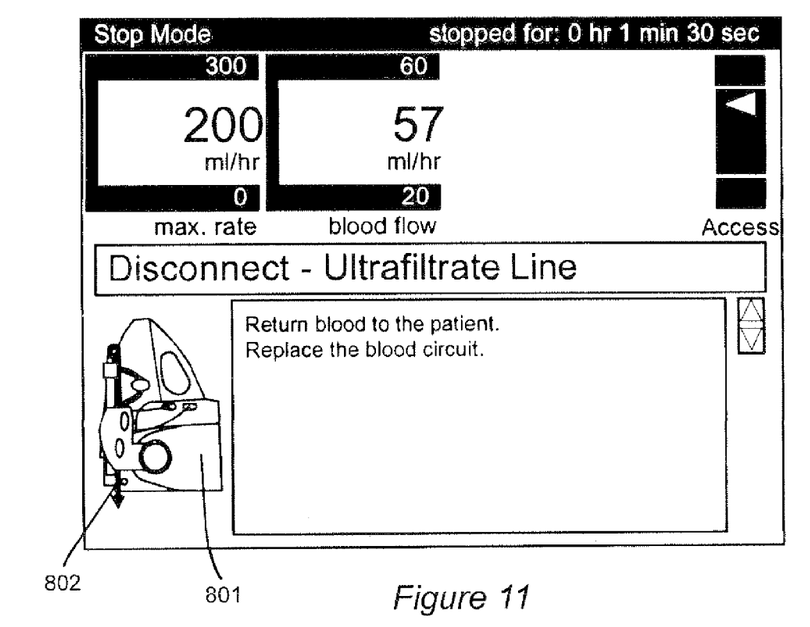
FIGS. 11 and 12 show a pictogram 801 of the system that detected a disconnection in the ultrafiltrate withdrawal line 802. A side view of the pump console is shown and the ultrafiltrate line is highlighted. Pictograph 803 of the system shows that there is a detected a jammed rotor of the blood pump 804. The pump element of the pictogram is highlighted and flashing. These are examples of screens with pictograms indicating disconnection of an ultrafiltrate line and jammed blood pump faults.
Figure 12:
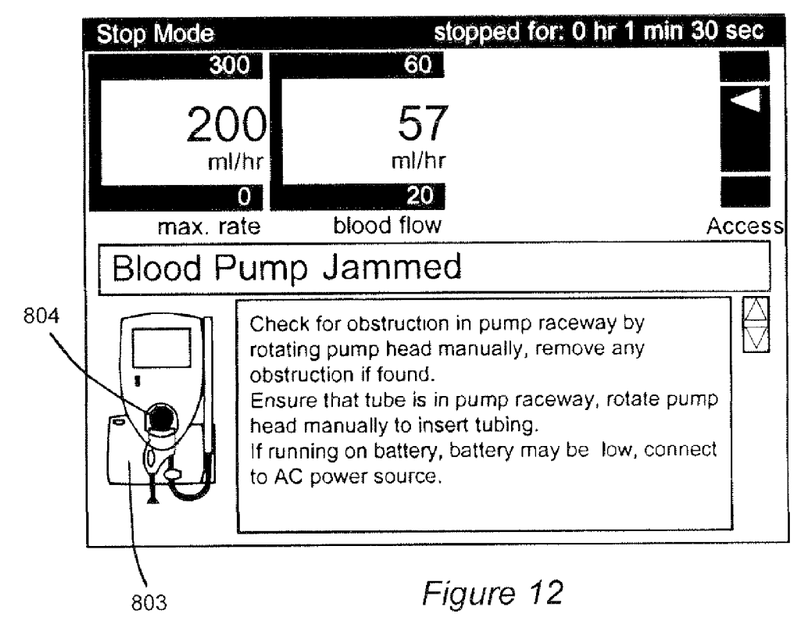

FIGS. 11 and 12 show a pictogram 801 of the system that detected a disconnection in the ultrafiltrate withdrawal line 802. A side view of the pump console is shown and the ultrafiltrate line is highlighted. Pictograph 803 of the system shows that there is a detected a jammed rotor of the blood pump 804. The pump element of the pictogram is highlighted and flushing.

Figure 13:
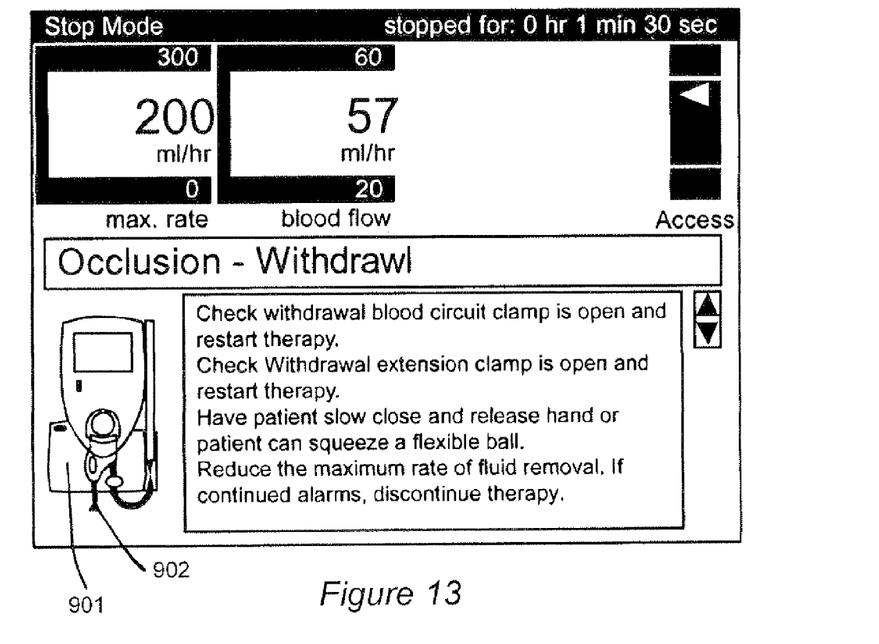
FIGS. 13 and 14 are examples of screens with pictograms indicating withdrawal bloodline occlusion and ultrafiltrate weight mismatch faults.
Figure 14:
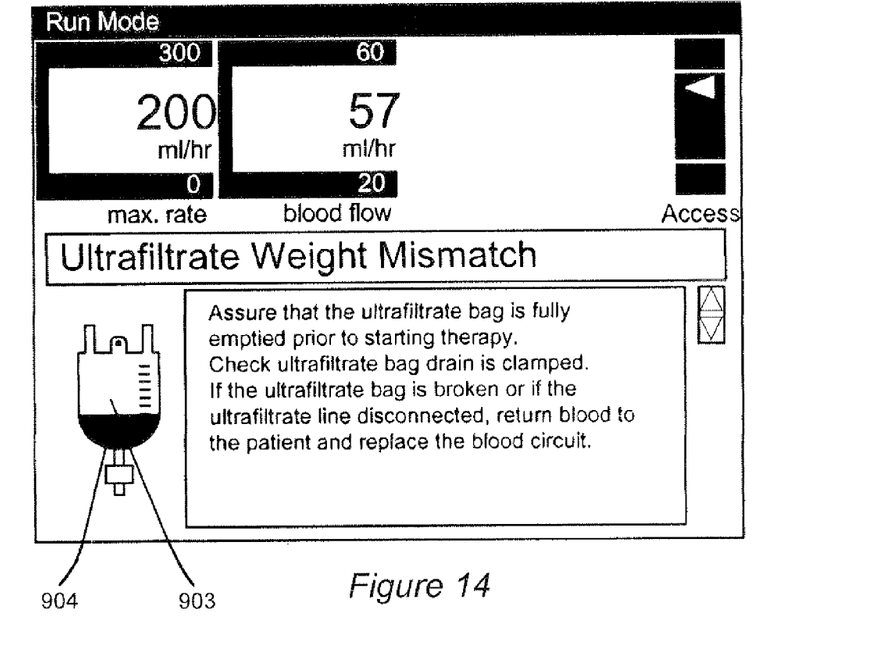

FIGS. 13 and 14 show a pictogram 901 of the system that has detected an occlusion in the blood withdrawal segment of the circuit. The withdrawal tubing 902 is flashing to attract the user's attention. The pictogram 903 shows the ultrafiltrate removal bag. The system has detected that the amount of fluid added to the bag does not correspond to the user setting, such as will occur when the bag is filled and needs replacement. The amount of fluid is detected by continuously weighing the ultrafiltrate collection bag. The fluid level 904 in the bag is flashing on the pictogram to attach the user's eye.

Figure 15:
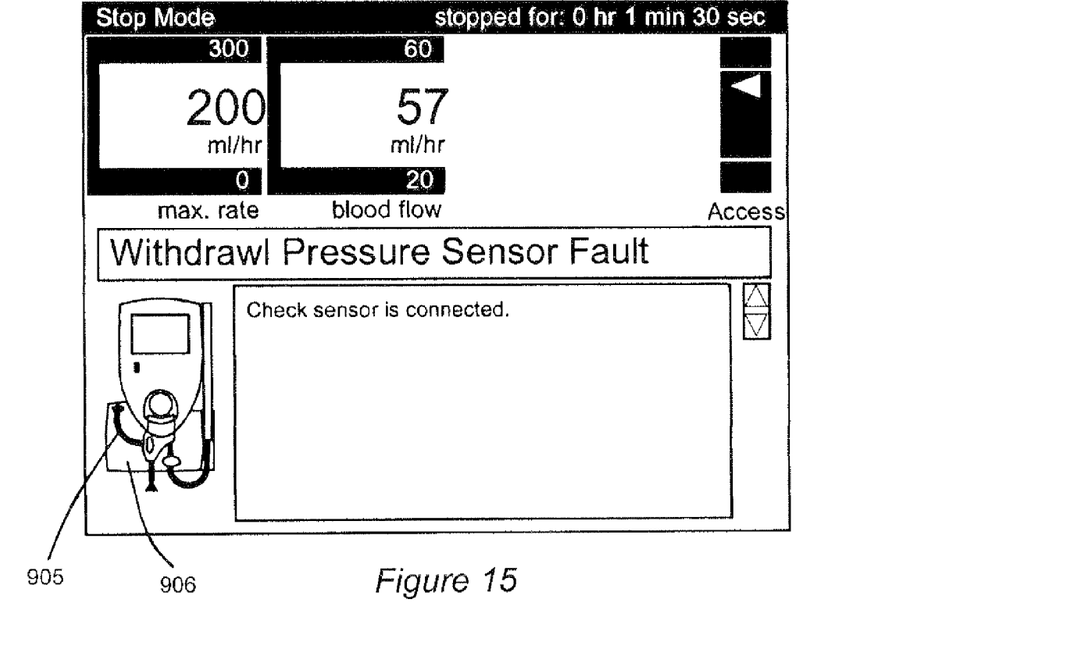
FIGS. 15 and 16 are examples of screens with pictograms indicating withdrawal pressure sensor and ultrafiltrate line occlusion faults.
Figure 16:
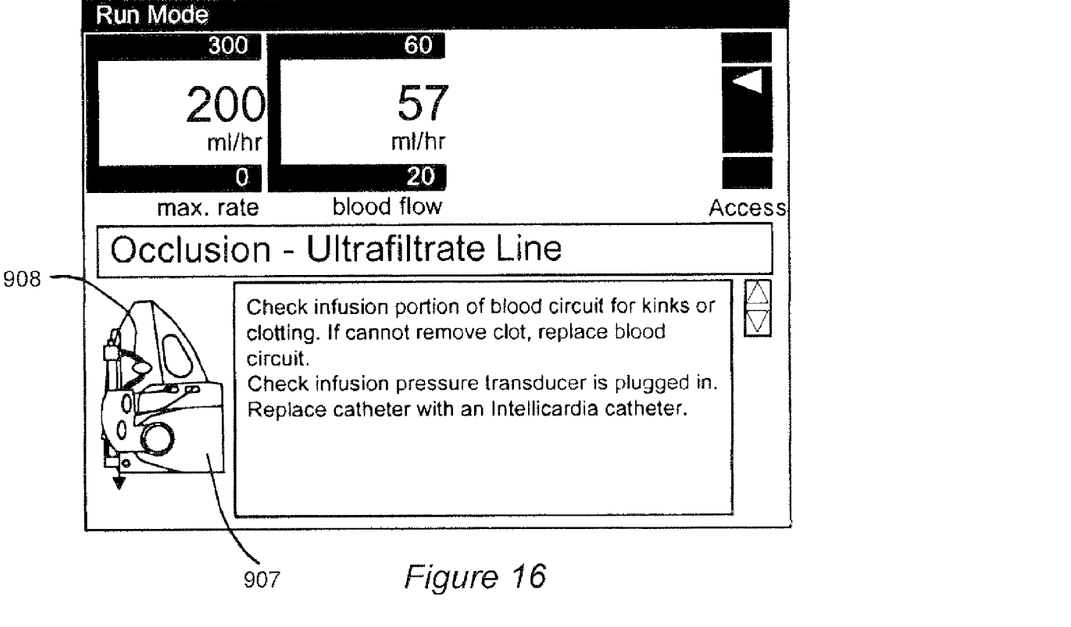

FIGS. 15 and 16 show a pictogram 906, of the system with an electrically disconnected or malfunctioning blood withdrawal pressure sensor. The electric disconnection of the sensor can be detected by the system by reading an abnormal voltage output from the sensor. The sensor connector and wire element 905 of the pictogram 906 is flashing. The pictogram 907 shows the system that detected occlusion in the ultrafiltrate removal line between the hemofilter and the ultrafiltrate pump. The ultrafiltrate segment of tubing 908 in the fluid path is flashing.

FIG. 17 illustrates the electrical architecture of the ultrafiltration controller system 200 (Part of 100 in FIG. 1), showing the various signal inputs and actuator outputs to the controller. The user-operator inputs the desired ultrafiltrate extraction rate into the controller by pressing buttons on a membrane interface keypad 125 on the controller. Other user settings may include the maximum flow rate of blood through the system, maximum time for running the circuit to filter the blood and the maximum ultrafiltrate rate. The settings input by the user are stored in a memory and read and displayed by the controller CPU 205 (central processing unit, e.g., microprocessor or micro-controller) on the LCD screen 127. CPU 205 is equipped with memory system 209 where software code and data are stored.

The controller CPU regulates the pump speeds by commanding a motor controller 202 to set the rotational speed of the blood pump 122 to a certain speed specified by the controller CPU. Similarly, the motor controller adjusts the speed of the ultrafiltrate pump 126 in response to commands from the controller CPU and to provide a particular filtrate flow velocity specified by the controller CPU.

Feedback signals from the withdrawal pressure sensor 112, ultrafiltrate pressure sensor 114 and blood return pressure sensor 113 are converted from analog voltage levels to digital signals in an A/D converter 216. The digital pressure signals are provided to the controller CPU as feedback signals and compared to the intended pressure levels determined by the CPU. This allows the CPU 205 software to detect disconnections and occlusions in the fluid path. In addition, the digital pressure signals may be read by the Safety system Processor 214. This ensures redundancy of critical safety monitoring functions of the system.

The motor controller 202 controls the velocity, rotational speed of the blood and filtrate pump motors 203, 204. Encoders 206 and 207 mounted to the rotational shaft of each of the motors as feedback provide quadrature signals (e.g., a pair of identical cyclical digital signals, but 90° out-of-phase with one another). These signal pairs are fed to a quadrature counter within the motor controller 202 to give both direction and position. The direction is determined by the signal lead of the quadrature signals. The position of the motor is determined by the accumulation of pulse edges. Actual motor velocity is computed by the motor controller as the rate of change of position. The controller calculates a position trajectory that dictates where the motor must be at a given time and the difference between the actual position and the desired position is used as feedback for the motor controller. The motor controller then modulates the percentage of the on time of the PWM signal sent to the one-half 218 bridge circuit to minimize the error. A separate quadrature counter is independently read by the Controller CPU to ensure that the Motor Controller is correctly controlling the velocity of the motor. This is achieved by differentiating the change in position of the motor over time. Additional source of information about the performance of the fluid path of the system are the digitized system voltages and currents 210. The CPU 205 can determine such events as a jammed pump 122 or 126 or an occluded filter 111 by continuously monitoring feedback from encoders 206 and 207 and current consumed by DC motors 203 and 204.

The CPU 205 monitors each of the critical signals, including signal indicative of blood leaks 155, pressures in blood circuit 112, 113 114, weight of filtrate bag 208, motor currents, air in bloodline detector 154 and motor speed/position. The CPU has stored in its memory safety and alarm levels for various operating conditions of the ultrafiltrate system. By comparing these allowable preset levels to the real-time operating signals, the Safety system Processor 214 can determine whether a safety alarm should be issued, and has the ability to independently stop both motors and reset the motor controller 202 and controller CPU 205 if necessary. It can also pinpoint the location of the alarm source along the fluid path of the machine.

Figure 18:
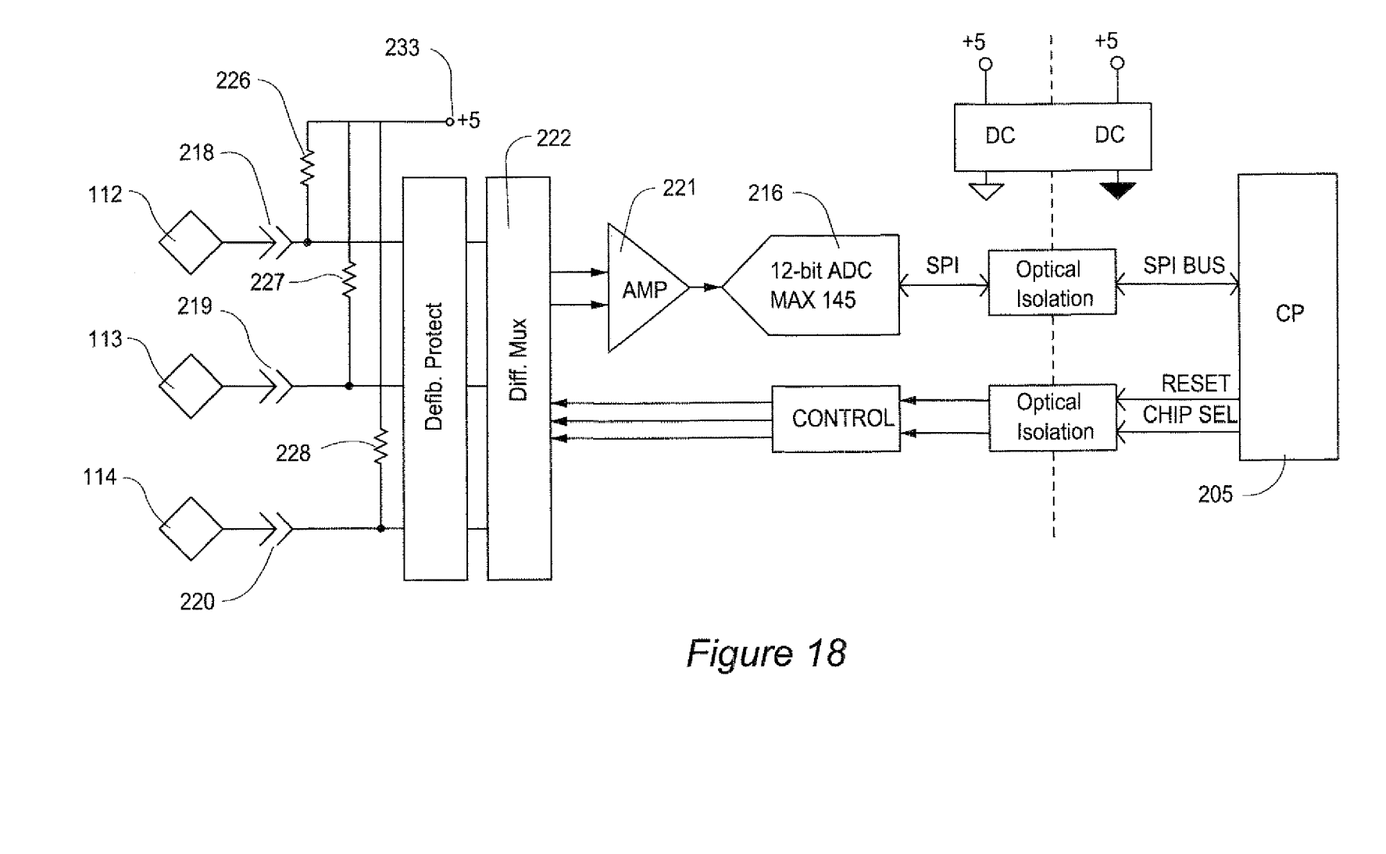

FIG. 18 shows the implementation of the electronics that enables the apparatus to detect if the plug-in disposable pressure sensors 112, 113 and 114 are electrically connected to the Console 100. Quick connectors 218, 219 and 220 are a part of the single use blood circuit 109 (See FIG. 1). They plug into receptacles that are electrically connected to the internal electronics of the apparatus. The pressure transducer connection scheme uses pull-up resistors 226, 227 and 228 to enable the Central Processor Unit (CPU) 205 to detect the connection of the pressure transducers. This ability is used to aid the user in troubleshooting and setup of the apparatus. The pull up resistors 226, 227 and 228 in the preferred embodiment are 10 MOhm. The electric resistance of pressure sensors 113, 114 and 115 is approximately 3 KOhm. It is essential that the resistance of pull-up resistors is substantially higher than the resistance of the sensors. This way when the sensors are connected the voltage source 233 does not contribute to the pressure reading by the CPU 205. By displaying a pictogram on the LCD screen the apparatus can request the user to connect a particular pressure transducer and switch to the next setup instruction when the connection has been performed.

When the disposable pressure transducers 112, 113 and 114 are not connected, the amplifier 221 is saturated with the 5 Volt DC voltage sources 233 and the CPU 205 reads 4,096 digital counts generated by the 12-bit ADC 216, which corresponds to greater than 600 mmHg pressure. This pressure is much higher than what can be normally expected by the machine. Therefore, when the CPU detects such high-pressure level, it can inform the user that a particular pressure sensor is unplugged or disconnected. By instructing the user to connect a specific pressure transducer 112, 113 or 114 the CPU 205 can detect when the transducer is connected by continuously measuring pressure, and waiting for the pressure to fall within an expected window.

Although the present invention has been described in terms of a particular embodiment, it is not intended that the invention be limited to that embodiment. Modifications of the disclosed embodiment within the spirit of the invention will be apparent to those skilled in the art. The scope of the present invention is defined by the claims that follow.

We claim:

1. A system for detecting an electrical sensor circuit comprising:
   a sensor signal processing circuit further comprising an input port, a signal line connecting the input port to the processing circuit, a pull-up resistor connected between the input port and a predetermined voltage, wherein said signal line is connected to an amplifier;
   a sensor circuit comprising a connector adapted to connect to the connector, wherein the sensor circuit has a resistance substantially less than the pull-up resistor, and
   wherein the sensor signal processing circuit detects an unconnected sensor based on the amplification of the voltage being outside a preset limit.

2. The system of claim 1 wherein the predetermined voltage is a voltage supply.

3. The system of claim 1 wherein the predetermined voltage is five (5) volts.

4. The system of claim 1 wherein the resistance of the pull-up resistor is at least three times the resistance of the sensor circuit.

5. The system of claim 1 wherein the resistance of the pull-up resistor is at least one Meg Ohm and the resistance of the sensor circuit is no greater than three Kilo Ohm.

6. The system of claim 1 wherein the pull-up resistor comprises a plurality of parallel pull-up resistors and each of the resistors is connected to different input port.

7. The system of claim 1 wherein the sensor circuit is on an extracorporeal blood circuit and the sensor signal processing circuit is included in a pump controller.

8. A system for detecting an electrical sensor circuit comprising:
   a sensor signal processing circuit further comprising an input to receive a connector to an output of the sensor circuit, a signal line connecting the input to the processing circuit, and a resistor connected between a signal line and a predetermined voltage;
   the sensor circuit comprising a connector adapted to connect to the input, wherein the sensor circuit has a resistance substantially less than the resistor, and
   wherein the sensor signal processing circuit detects an unconnected sensor circuit based on the voltage being outside a predetermined limit.

9. The system of claim 8 wherein the resistor is a pull-up resistor and the predetermined voltage is a voltage supply.

10. The system of claim 8 wherein the resistor is a pull-up resistor and the predetermined voltage is five (5) volts.

11. The system of claim 8 wherein the resistance of the resistor is at least three times the resistance of the sensor circuit.

12. The system of claim 8 wherein the resistance of the resistor is at least one Meg Ohm and the resistance of the sensor circuit is no greater than three Kilo Ohm.

13. The system of claim 8 wherein the resistor comprises a plurality of parallel resistors and each of the resistors is connected to different input port.

14. The system of claim 8 wherein the sensor circuit is on an extracorporeal blood circuit and the sensor signal processing circuit is included in a pump controller.

* * * * *